(12) United States Patent
Anson

(10) Patent No.: US 8,147,251 B1
(45) Date of Patent: Apr. 3, 2012

(54) COMPUTER-AIDED PSYCHOLOGICAL DIAGNOSIS AND TREATMENT SYSTEM

(76) Inventor: Wendy C. Anson, Encino, CA (US)

( * ) Notice: Subject to any disclaimer, the term of this patent is extended or adjusted under 35 U.S.C. 154(b) by 1661 days.

(21) Appl. No.: 11/388,719

(22) Filed: Mar. 23, 2006

(51) Int. Cl.
*G09B 11/00* (2006.01)
(52) U.S. Cl. .......................... 434/236; 434/365; 434/112
(58) Field of Classification Search .................. 600/300; 434/236, 118, 112, 365
See application file for complete search history.

(56) References Cited

U.S. PATENT DOCUMENTS

| | | | | |
|---|---|---|---|---|
| 5,169,342 A | * | 12/1992 | Steele et al. .................. | 434/112 |
| 5,742,779 A | * | 4/1998 | Steele et al. .................. | 345/660 |
| 5,748,177 A | * | 5/1998 | Baker et al. .................. | 434/112 |
| 5,890,905 A | * | 4/1999 | Bergman ....................... | 434/236 |
| 6,097,927 A | * | 8/2000 | LaDue .......................... | 434/236 |
| 7,357,639 B2 | * | 4/2008 | Stillman ....................... | 434/112 |

* cited by examiner

*Primary Examiner* — Kathleen Mosser
(74) *Attorney, Agent, or Firm* — Thomas I. Rozsa

(57) ABSTRACT

A psychological testing and treatment system according to the present disclosure employs a computer to provide objective, unbiased language, independent interaction with users to circumvent natural human psychological defenses and gather information about traumatic or troubling events of the user. A user's interaction with relevant icons permits the computer to gather data to permit diagnosis and treatment. At the same time, the system enables the extraction, archiving and measurement of this data from the user. Subsequent and consequent to this communication via the system, the disturbance in the user is ameliorated to a degree by virtue of the interaction.

3 Claims, 21 Drawing Sheets

COMPUTER-AIDED PSYCHOLOGICAL DIAGNOSIS AND TREATMENT SYSTEM

BACKGROUND OF THE INVENTION

1. Field of the Invention

The present system relates generally to a computer-implemented psychological diagnosis, and more specifically it relates to a computer-implemented treatment, diagnostic and communications system for selecting and engaging with, and communicating about, troubling and/or traumatic psychological material.

2. Description of the Prior Art

For years therapists, doctors and others working with children and adults who had been through highly disturbing experiences have been trying to diagnose, treat and communicate with these individuals about the disturbing experiences. They have asked questions, both open-ended and specific, on the individual's feelings and experiences; those current, and those which led up to the current condition of disturbance or the condition of being unable to communicate about the experience, with largely unsuccessful results.

However, present theoretical hypotheses and clinical findings alike have shown that adults and children who have undergone highly disturbing experiences are not able to talk about them; sometimes, not even able to remember them. For this reason, questionnaires and other means to get data from these individuals through standard expressive language have been highly inadequate.

Protective mechanisms within the human psyche predictably take the memory of highly disturbing or traumatic experiences away; or, alternatively, freeze the psyche with the memory of the disturbing event in an intrusive "takeover" that floods the individual with the feelings and thoughts associated with the overwhelming past incident. Yet, in order for the therapist or fellow communicator to communicate with the troubled individual or access this data, the adult or child must be able to communicate the events of the disturbance, i.e., these incidents in this order. Further, in order for treatment of the incommunicative and/or disturbed state to be ameliorated, the individual needs to have access to "these incidents in this order", i.e., exactly what happened. However, traditional therapeutic or communicative means have not worked, precisely because the psychic response to highly disturbing incidents, experienced or witnessed, is either to (a) shut down (no memory, thus no ability to "tell about") or (b) flood the individual with the terrible feeling(s) surrounding a single, frozen in-time, very small part of the disturbing event (no ability to access the "before" the incident and the "after" the incident, thus no ability to access and "tell").

A diagnostic and treatment tool for children in the prior art has been the sand-tray (known also as "sandbox", "sand play", "sandplay", "play and water activity table", "play therapy mat for projective doll play" "therapy play stage", "doll house", but to be called "sand tray" here) and male and female adult and child dolls fitted with clothing that can be applied and removed.

The main problems with conventional treatment and diagnosis protocols linked with the "sandbox", "sand-play", etc., are not only that they require full memory and expressive language capability such as oral interviews or elicited self-reports but also that they are not uniform, universal, precise indicators of a patient's/user's problems. They are often subjective, transient and not automatically entered into a data system which automatically calculates, tracks and times patient/user responses according to universal measures previously established.

What is needed is a system that promotes objective, unbiased interaction with patients to help understand, diagnose and treat traumatic and/or highly disturbing experiences. In these respects, the present psychological treatment and diagnostic system substantially departs from the conventional concepts and designs. It provides a system primarily developed for the purpose of accessing previously inaccessible data as described above, uniformly and precisely eliciting indicators of a patient's/user's problem and automatically entering them into a data system. The data system automatically calculates, tracks and times patient/user responses according to universal measures of disturbance and/or trauma previously established through best practices, and construct-approved statistical testing, and subsequently indicates a profile of the user/patient along a spectrum of disturbance and/or trauma.

SUMMARY OF THE INVENTION

Through specially engineered and designed technology, the present system solves the problem of getting the individual both to access and to communicate the disturbing events in chronological order.

The system and method of this system is able to work around the shortcomings of traditional question-answer, self-report processes of conscious, cognitive expressive language. Instead of using a traditional communications strategy, the system is able to pass by the conscious defenses and access the unconscious, non-verbal part of the child's or adult's psyche to access the memory of what happened when and how it happened. Further, the special design and technology enables the child or adult to "tell about" or communicate "what happened when".

Adult and child Post Traumatic Stress Disorder (PTSD) sufferers are not psychically or cognitively equipped to make use of or access cognitive processes around the traumatic event. This is the event that has caused either overwhelming flooding or complete numbing in reaction to it, which is the inevitable, predictable and normal human reaction-response to a traumatic event: an overwhelming, horrific action or occurrence which happens to or is witnessed by the subject who is powerless to stop it. Both intrusive, repetitive flooding of emotion around the event (the "re-occurring flashback") as well as the complete numbing off from (emotional impairment) or factual forgetting of (cognitive impairment) makes accessing the full, complete "story" of the trauma, "these events in this order", impossible to do for the adult or child victim of PTSD. Yet for the therapist to begin to understand the problem and event in order to be able to undertake therapy, and for the sufferer to fully access the event in its entirety (chronological sequence of exactly what happened attached to the full accompanying emotions at each stage), the sufferer must have access to the full and complete "story". The sufferer must access the story before he/she can access the accompanying emotions and achieve cognitive understanding of the event and subsequently and consequently, achieve the catharsis of emotions necessary for amelioration of the disorder.

An object of the present system is to help to treat and diagnose psychological distress, disturbance and/or trauma in adults and in children by the system described here of the user interacting with relevant icons which permits the computer to gather data to permit diagnosis and treatment.

Another object is to plan a psychological treatment and diagnostic system that can automatically track and calculate patient/user indices of distress or trauma and emerge with a "profile" of distress and/or trauma along a pre-determined spectrum of distress/trauma.

Another object is to provide a psychological treatment and diagnostic system that provides a more systematic, universal and objective method/means of obtaining and tracking user/patient data in terms of communicating previously incommunicable data.

Another object is to provide a psychological treatment and diagnostic system that will function for patients/users who are pre-linguistic or have some sort of problem with expressive language and thus with communicating indices of their distress or trauma with the therapist or facilitator.

Another object is to provide a means of a patient's "telling the story" of the disturbing event that happened to them non-verbally and non-linguistically, but instead by moving various icon/sound objects in a sequence of their choice.

Another object is to have a lightweight, portable apparatus that the operator/clinician can take to various user sites.

Another object is to have sets of interchangeable icon-objects that conform to or are compatible with the individual user's environment.

Other objects and advantages of the present system will become obvious to the reader and it is intended that these objects and advantages are within the scope of the present system.

To the accomplishment of the above and related objects, the system may be embodied in the forms illustrated in the accompanying drawings, attention being called to the fact, however, that the drawings are illustrative only, and that changes may be made in the specific construction illustrated.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
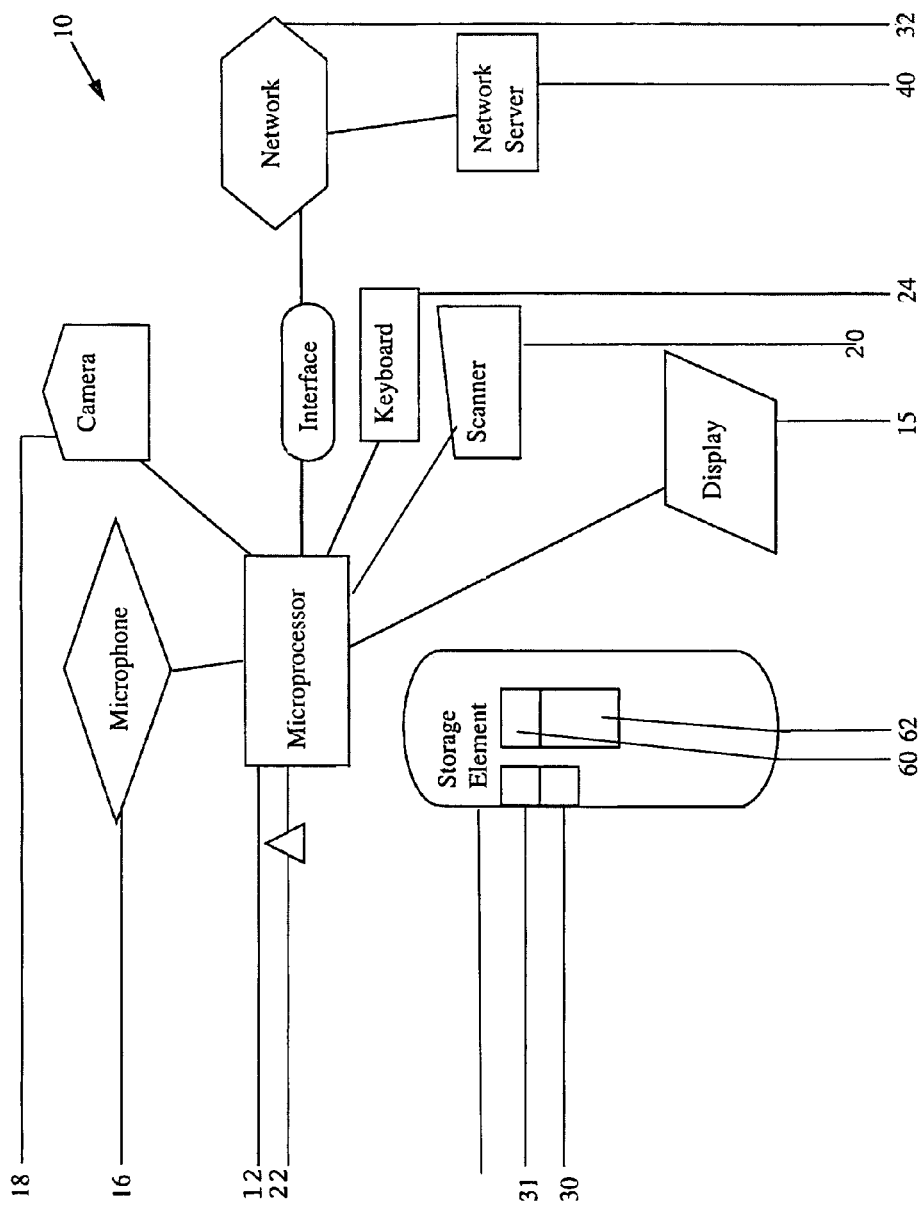
FIG. 1 is a block diagram of an exemplary computer system utilizing the present system.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is a psychological testing and treatment system according to the present disclosure that employs a computer to provide objective, unbiased language, independent interaction with users to circumvent natural human psychological defenses and gather information about traumatic or troubling events of the user. A user's interaction with relevant icons permits the computer to gather data to permit diagnosis and treatment. At the same time, the system enables the extraction, archiving and measurement of this data obtained from the user. Subsequent and consequent to this communication via the system, the disturbance in the user is ameliorated to a degree by virtue of the interaction.

A computer-implemented system according to the present disclosure has an interface and data system which allows the user to choose, place and "play" in sequence sound-embellished icons (FIGS. 4-20), and a data "back end" (FIGS. 1-3) which allows the tracking, timing and computation of the icon manipulation and placement. The icons are weighted according to a scale indicative of trauma or disturbance intensity and user selection of these "scored" icons is subsequently computed and scored by the system. In view of the foregoing disadvantages inherent in the known types of psychological treatment, diagnostic and communications tool now present in the prior art, the present invention provides a new psychological treatment and diagnostic system construction. In this system, the same can be utilized for eliciting indicators of a patient's/user's problem and automatically entering them into a data system which automatically calculates, tracks and times patient/user responses according to universal measures of disturbance and/or trauma previously established through best practices, and construct-approved statistical testing, and subsequently indicates a profile of the user/patient along a spectrum of disturbance and/or trauma.

The general purpose of the present system, which will be described subsequently in greater detail, is to provide a new psychological treatment, diagnostic and communication tool that has many of the advantages of the psychological treatment and diagnostic tools mentioned heretofore and many novel features that result in a new psychological treatment and diagnostic tool system which is not anticipated, rendered obvious, suggested, or even implied by any of the prior psychological treatment and diagnostic art, either alone or in any combination thereof.

To attain this, the present system generally comprises an interactive multimedia computer interface, and a software tracking program connected to the interface and the keystrokes made thereupon. The computer interface is comprised of objects connected to sounds which can be selected, manipulated and moved freely to an alternatively highlighted series of "squares" which contain the selected icons when they are moved across and finally within the squares' outlines. The tracking software times and records and then launches a separate data file which describes the entire sequence of the user/patient's choice and movement of the icon/sound objects. The range, field or collection of icon/sound objects on the desktop as appropriate for the individual patient can be selected by the therapist via deletion, addition, or exchange.

There has thus been outlined, rather broadly, the more important features of the system in order that the detailed description thereof may be better understood, and in order that the present contribution to the art may be better appreciated. There are additional features of the system that will be described hereinafter.

In this respect, before explaining at least one embodiment of the system in detail, it is to be understood that the system is not limited in its applications to the details of construction and to the arrangements of the components set forth in the following description or illustrated in the drawings. The system is capable of other embodiments and of being practiced and carried out in various ways. Also, it is to be understood that the phraseology and terminology employed herein are for the purpose of the description and should not be regarded as limiting.

A psychological diagnosis and treatment system according to the present disclosure works by engaging users on a preconscious level, getting past the conscious psychic defenses by first engaging the subject with the display of randomly highlighting inanimate and animate objects. Once having engaged them, the system keeps them on task through the launch of the four alternatively highlighting boxes into which the user is invited to seemingly inadvertently and randomly pick and place the icons of choice representing the pieces of the traumatic incident.

Turning now descriptively to the drawings, in which similar reference characters denote similar elements throughout the several views, the attached figures illustrate a psychological treatment, diagnostic and communications system, which comprises an interactive multimedia computer interface, and a data tracking software which interfaces seamlessly with the computer interface. The interactive multimedia computer interface is comprised of algorithms which record in real time and sequence the actions and events performed on the interactive multimedia computer interface through movements of the cursor made by the patient/user.

The interactive multimedia computer interface is computer programming and consists of jpg icons and midi sounds, although any suitable formats may be used.

Referring now to FIG. 1, computer-implemented psychological testing and treatment system 10 includes microprocessor 12 connected to storage element 14, display 15, and one or more interface or interaction elements such as microphone 16, camera 18 and scanner 20. Pointing devices such as mouse 22 and keyboard 24 may also be included. Diagnostic and treatment software 30 may be stored in storage element 14 local to microprocessor 12 or it may be run from a network server 40 across network 32 such as a LAN or any other suitable network such as the internet.

Figure 2:
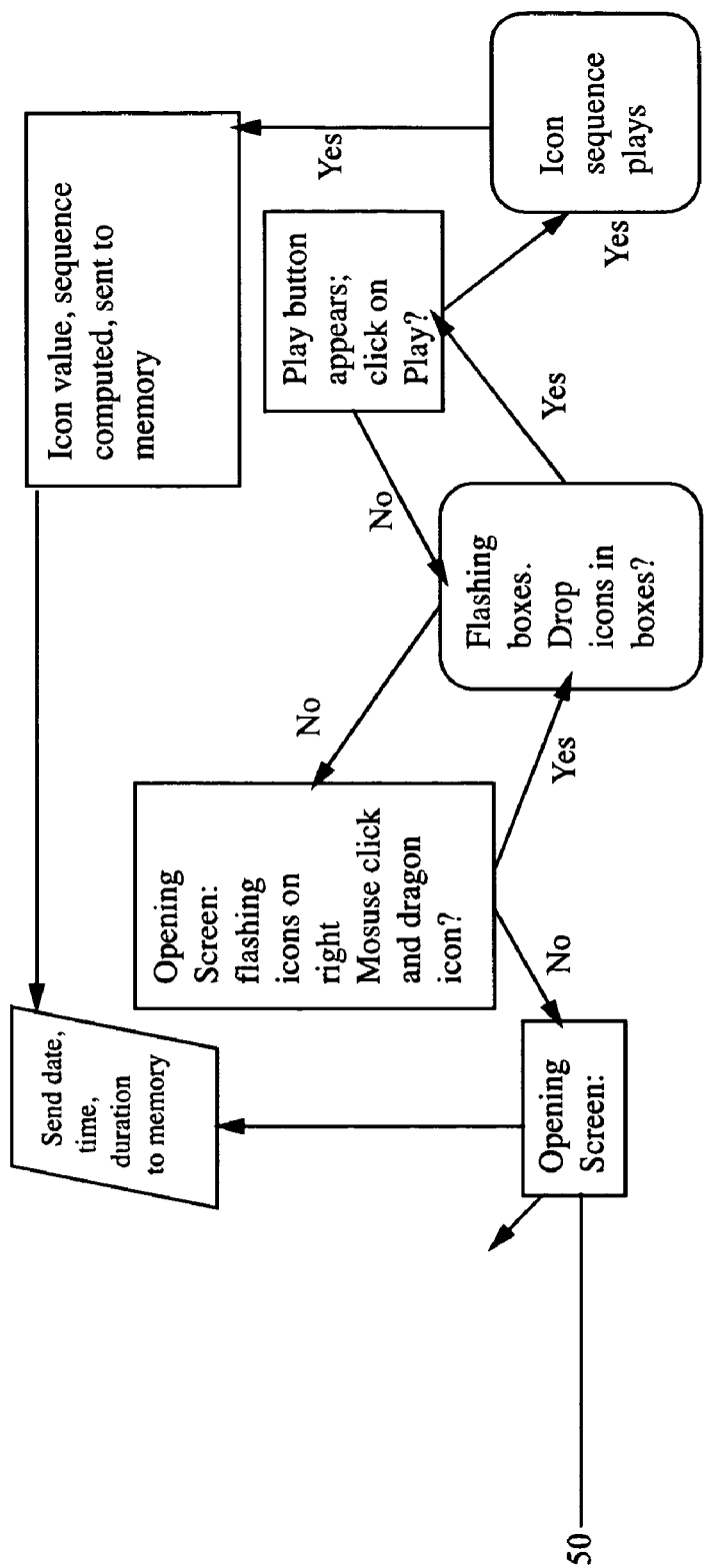
FIG. 2 is a flow chart illustrating an overall process of the present system.
Figure 4:
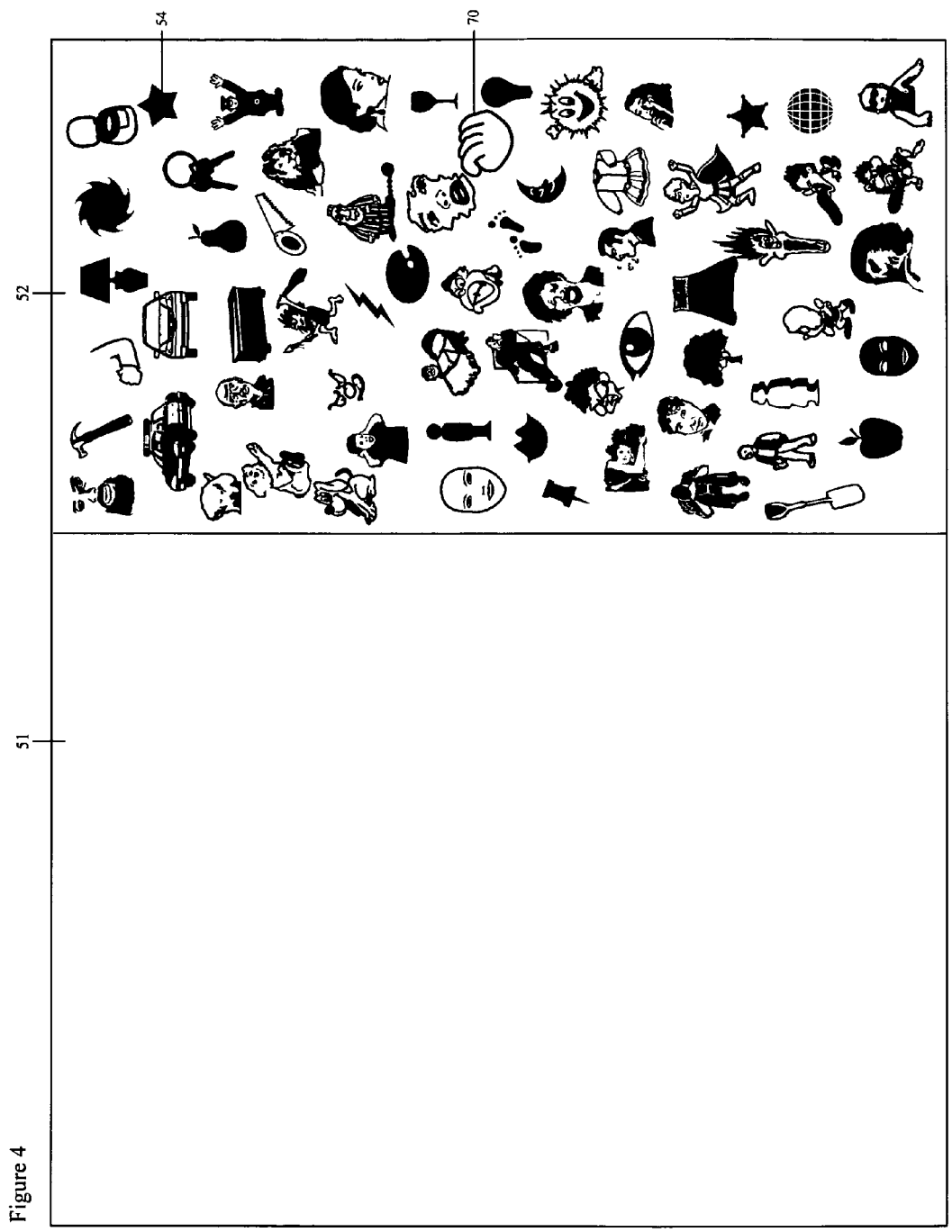
FIG. 4 displays the entire field of the user interface having a diagnostic field and an icon field.

Referring now to FIGS. 1, 2 and 4, diagnostic and treatment software 30 is launched either on local microprocessor 12 or from a remote host (not shown). Upon launch at step 50, opening screen, shown in FIG. 4, becomes visible on display 15. A user is able to explore object icon field 52 containing one or more relevant object icons such as icon 54, by using any suitable pointing device such as mouse 22 to cause cursor 70 to move within field 52. As cursor 70 encounters an icon such as icon 54 a timer 31 is launched and data 60 is saved into database 62. Data 60 may contain relevant parameters such as time of encounter, duration of encounter; direction of movement at encounter, direction of movement at termination of encounter and any other suitable parameters.

Figure 3A:
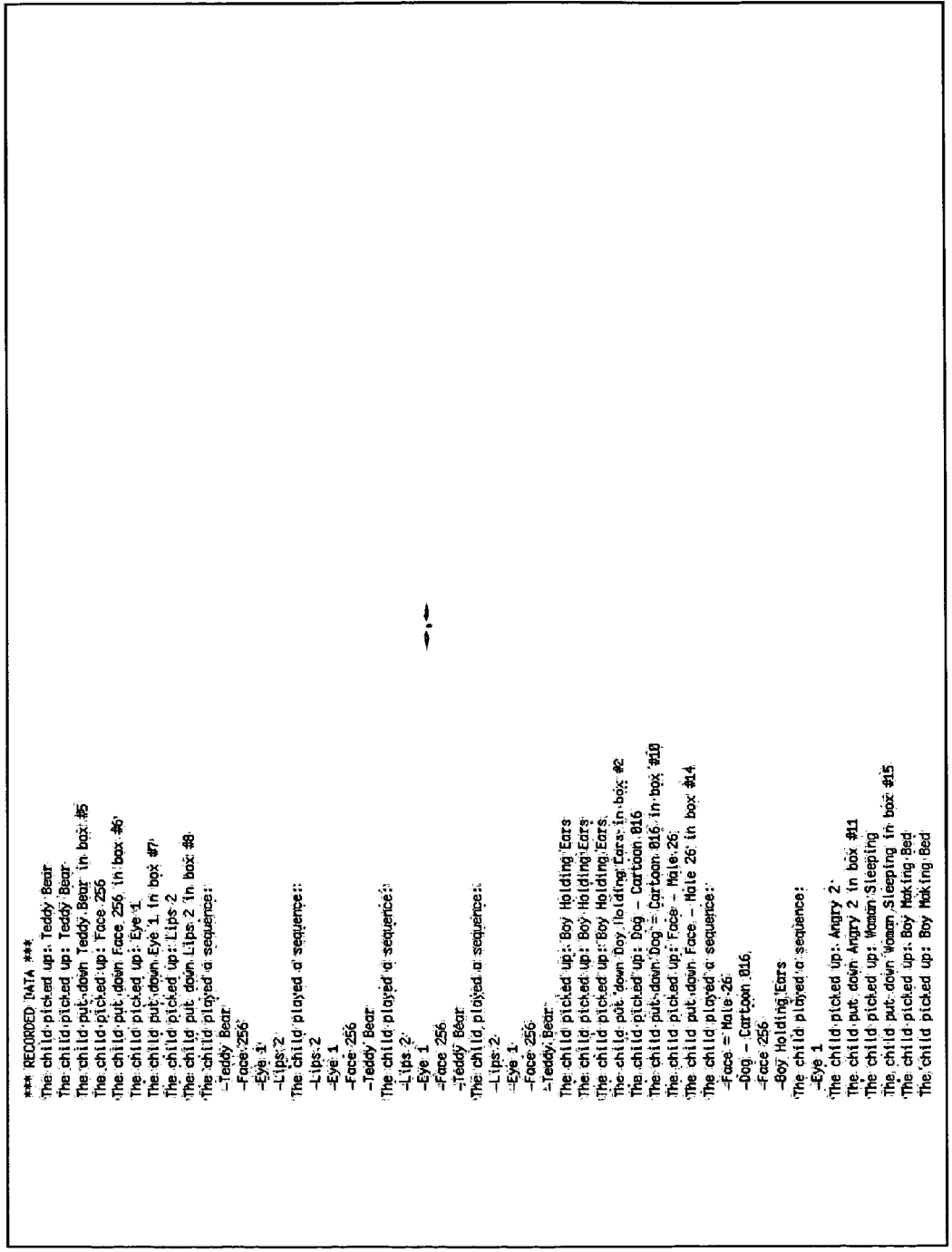
FIG. 3A is one exemplary data file from the application of the system.
Figure 3B:
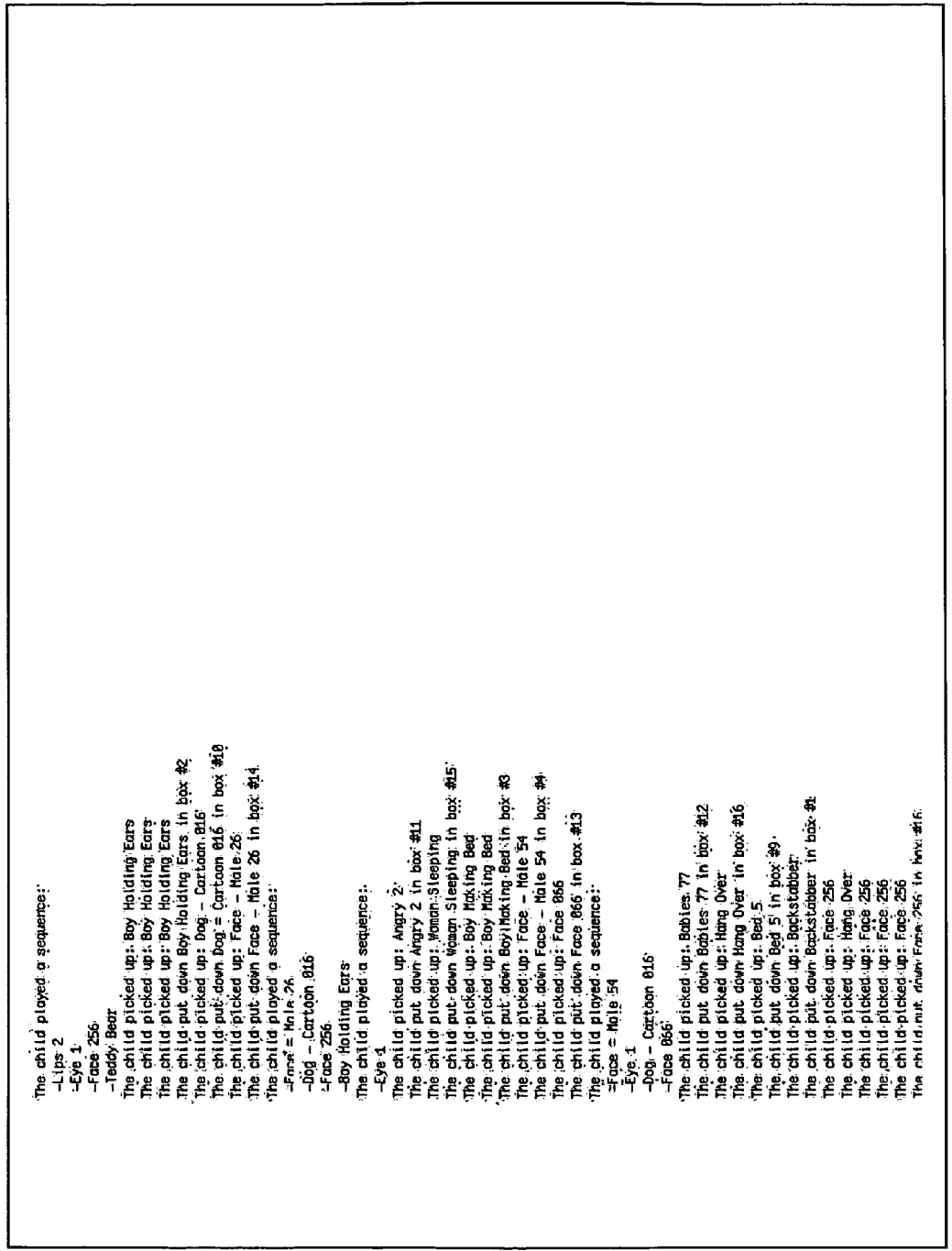
FIG. 3B is the continuation of the exemplary data file from FIG. 3A.

Referring now to FIGS. 3A and 3B, contents of data 60 file include parameters such as time, sequence of user pick-ups and put-downs of icons as well as order and content of icon sequence encounters.

Referring now to FIG. 4, there can be seen the user interface has two sections: a diagnostic field 51 and an icon field 52. Within the icon field 52, a user is able to explore icon field 52 containing one or more relevant icons such as exemplary icon 54, by using any suitable pointing device such as mouse 22 to cause cursor 70 to move within icon field 52.

Figure 5:
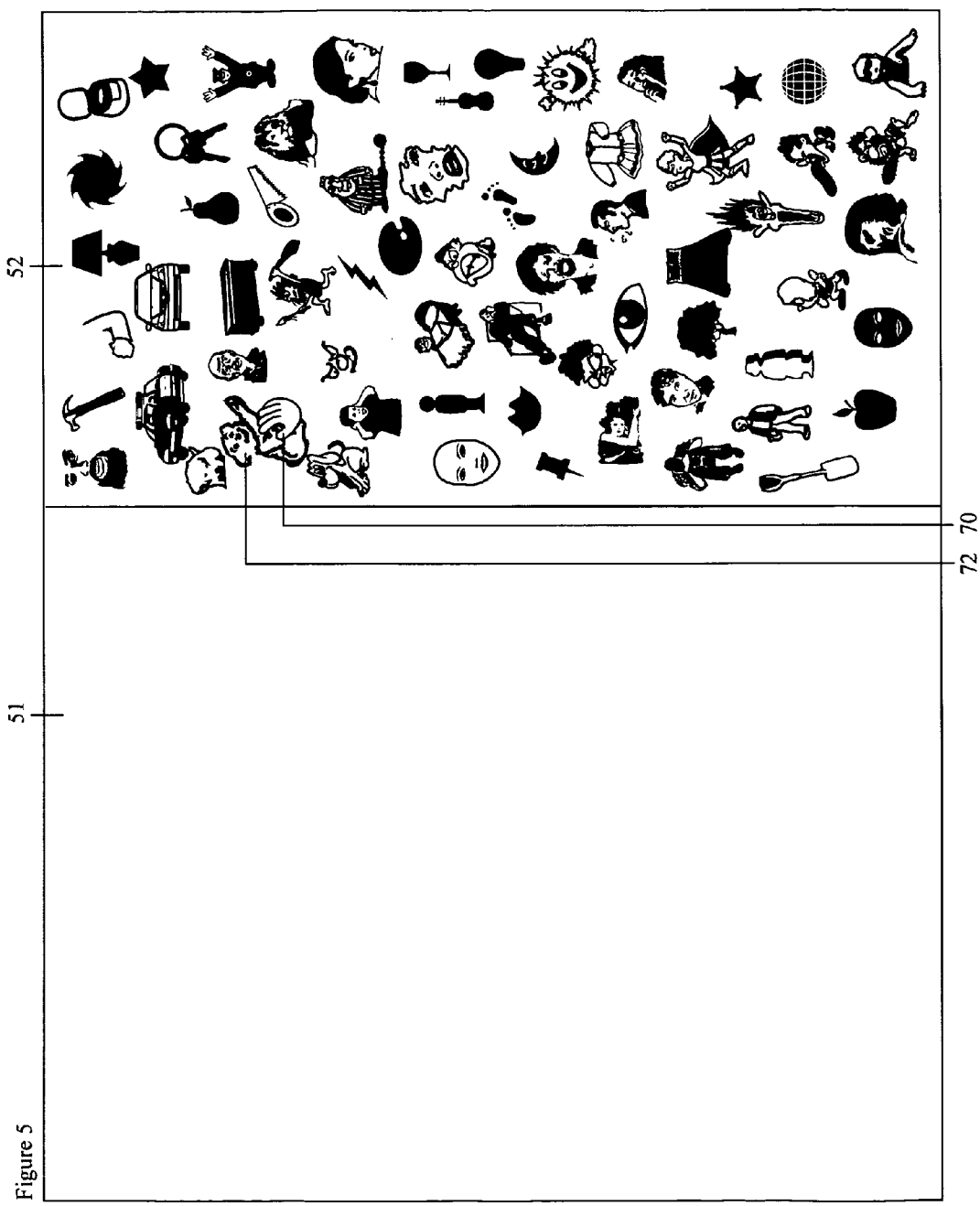
FIG. 5 displays the user interface, wherein the cursor is selecting an exemplary icon.

Referring now to FIG. 5, cursor 70 encounters an icon such as icon 72 which enlarges and simultaneously a unique sound is emitted.

Figure 6:
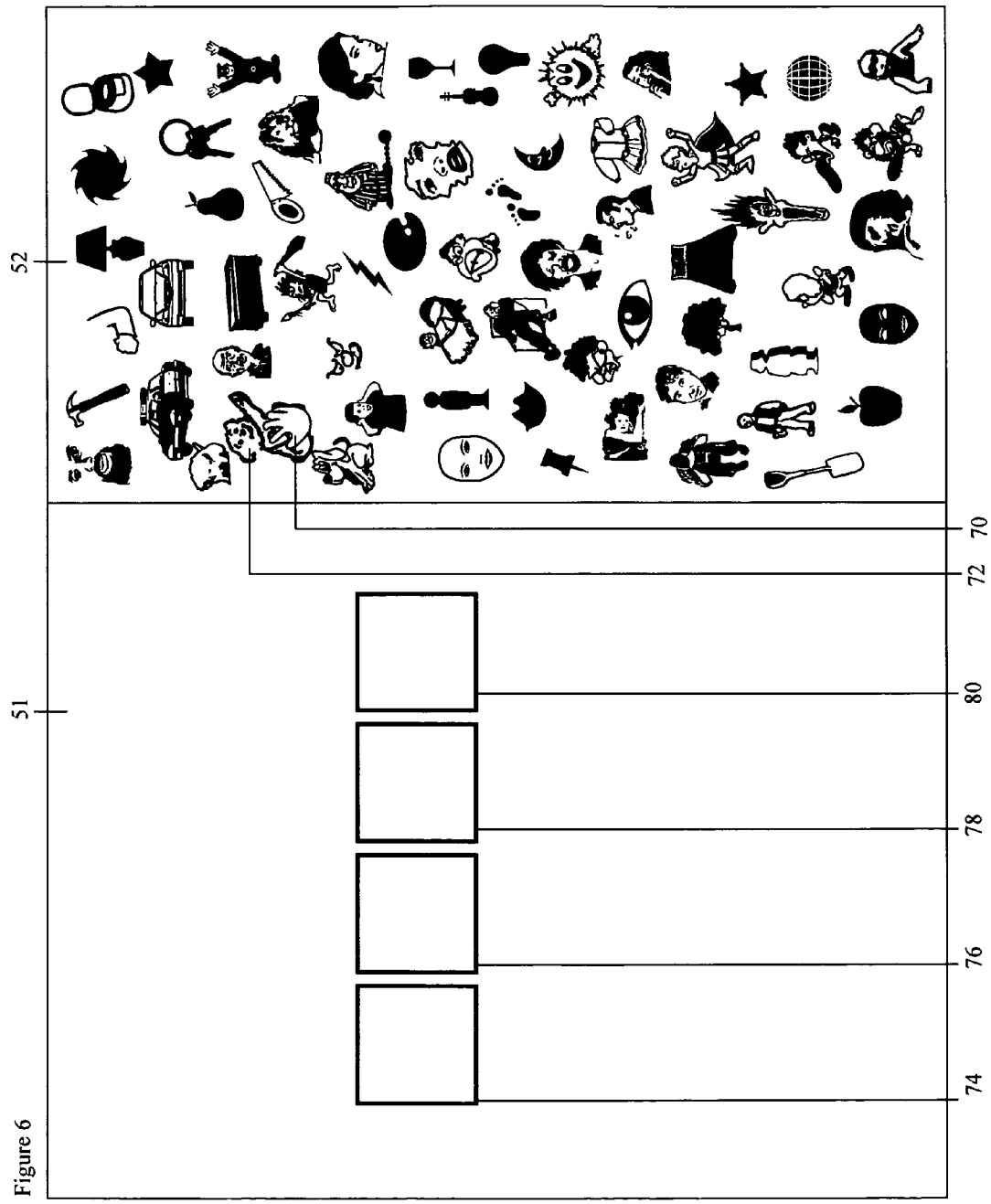
FIG. 6 displays the four squares within the diagnostic field of the user interface that are launched upon the selection of a first exemplary icon.

Referring now to FIG. 6, cursor 70 encounters another exemplary icon such as koala icon 72 and launches squares 74, 76, 78, 80 in diagnostic field 51 on the screen which all highlight in turn and in repeating cycle.

Figure 7:
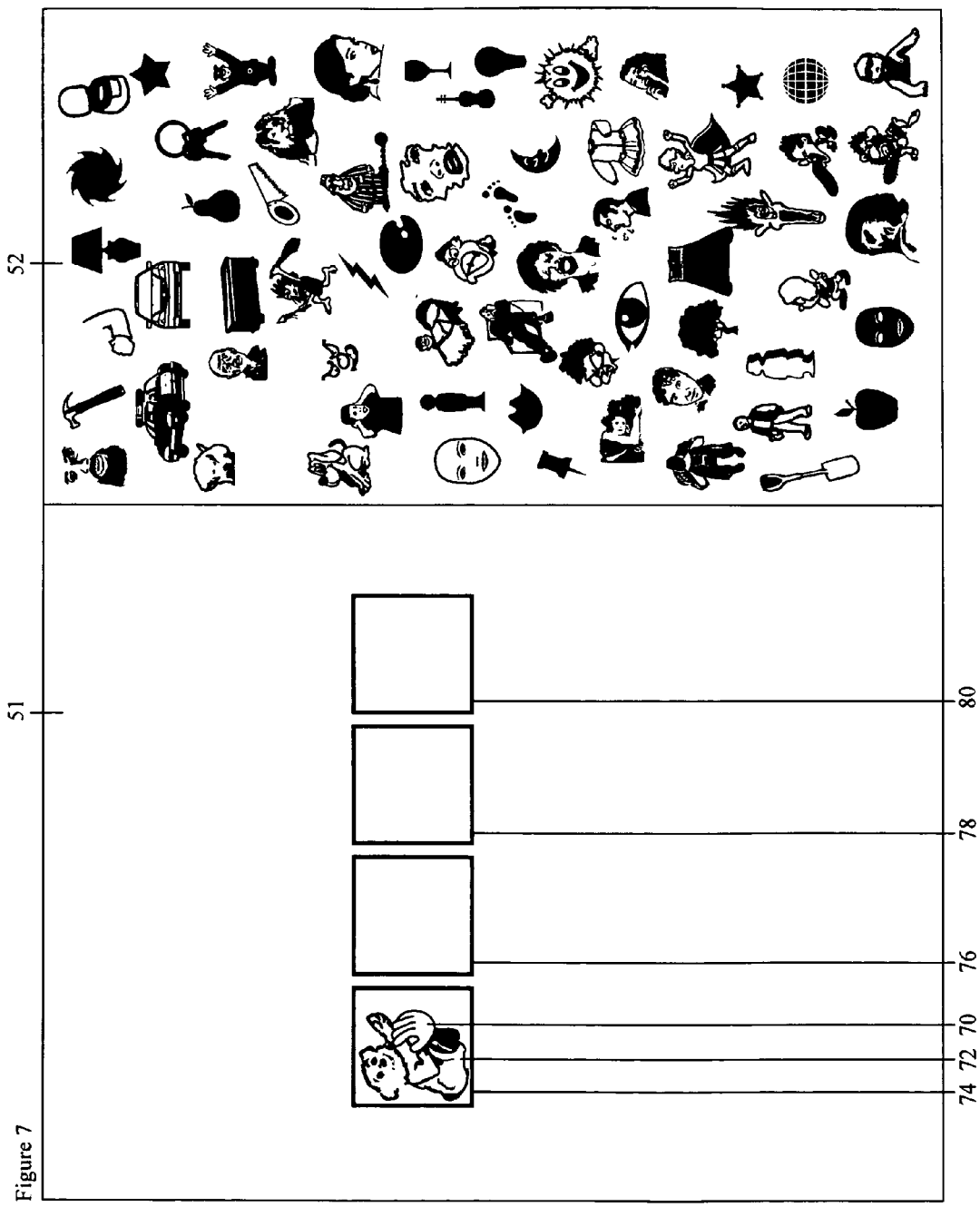
FIG. 7 displays an icon placement by the cursor within the first square within the diagnostic field of the user interface.

Referring now to FIG. 7, cursor 70 encounters an icon such as koala icon 72 from icon field 52 which is placed in any of the four squares 74, 76, 78, 80, and is shown being placed in, for example, square 74 in diagnostic field 51.

Figure 8:
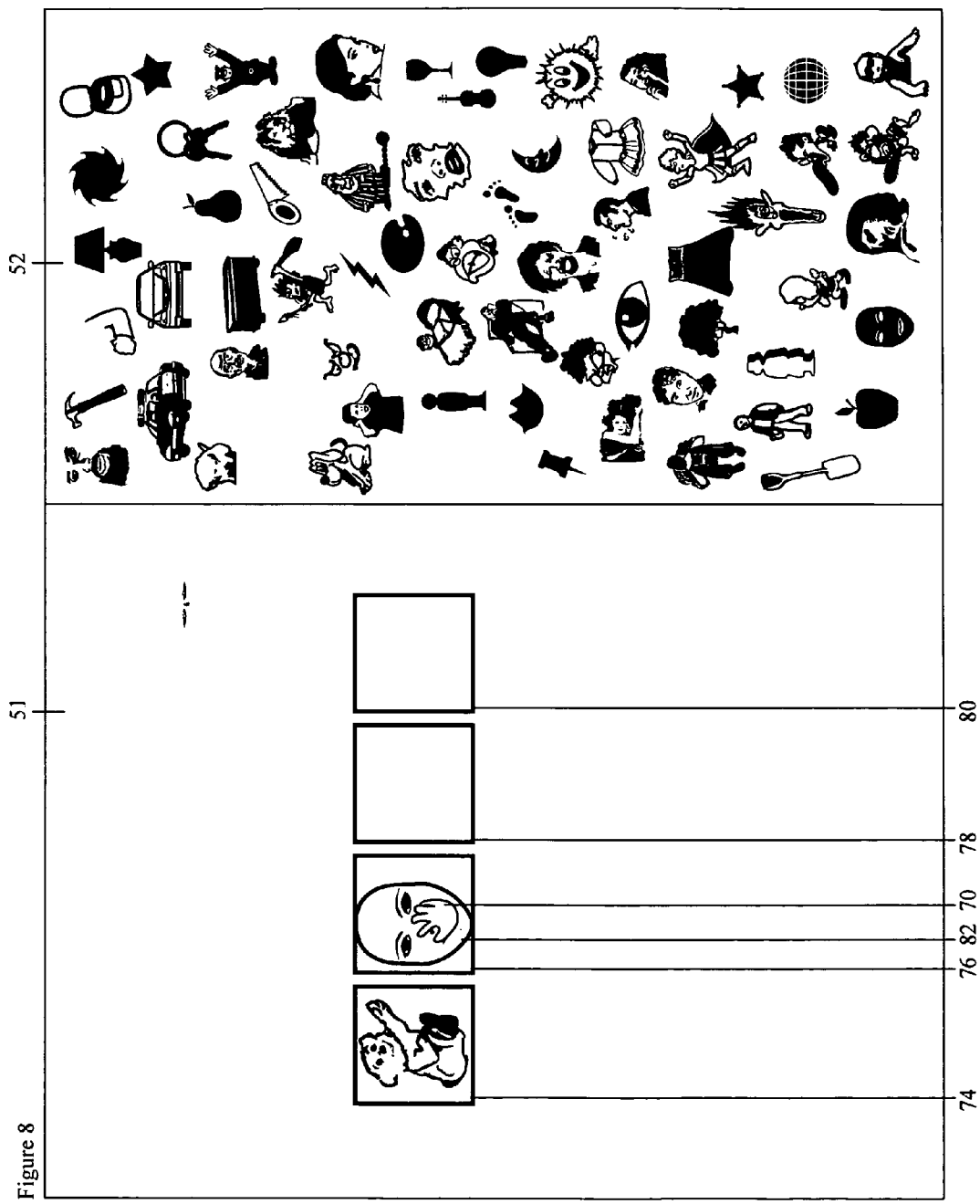
FIG. 8 displays an icon placement by the cursor within the second square within the diagnostic field of the user interface.

Referring now to FIG. 8, an icon such as face icon 82 from icon field 52 is moved onto any square in diagnostic field 51, for example, square 76.

Figure 9:
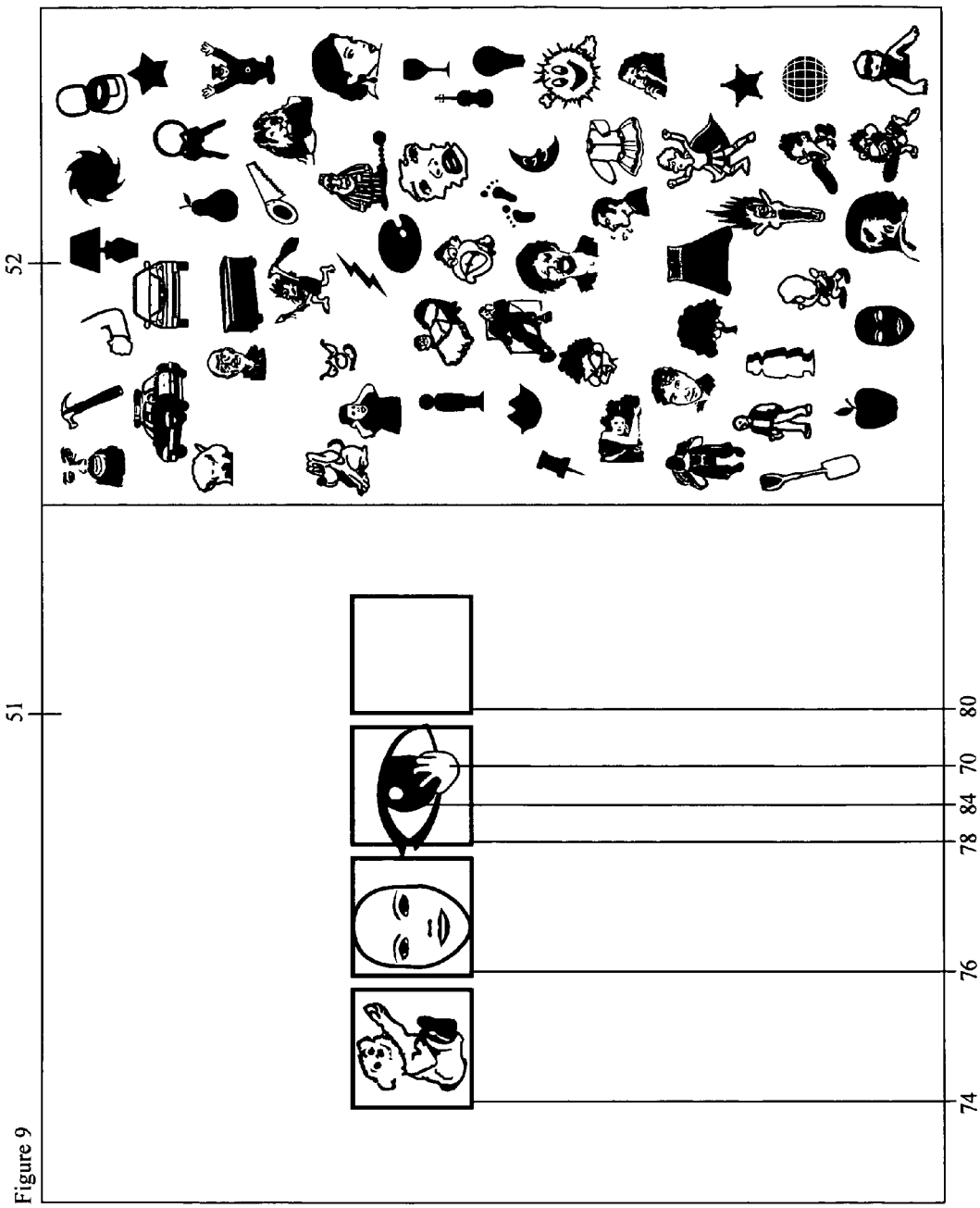
FIG. 9 displays an icon placement by the cursor within the third square within the diagnostic field of the user interface.

Referring now to FIG. 9, an icon such as eye icon 84 from icon field 52 is placed on any square in diagnostic field 51, for example, square 78.

Figure 10:
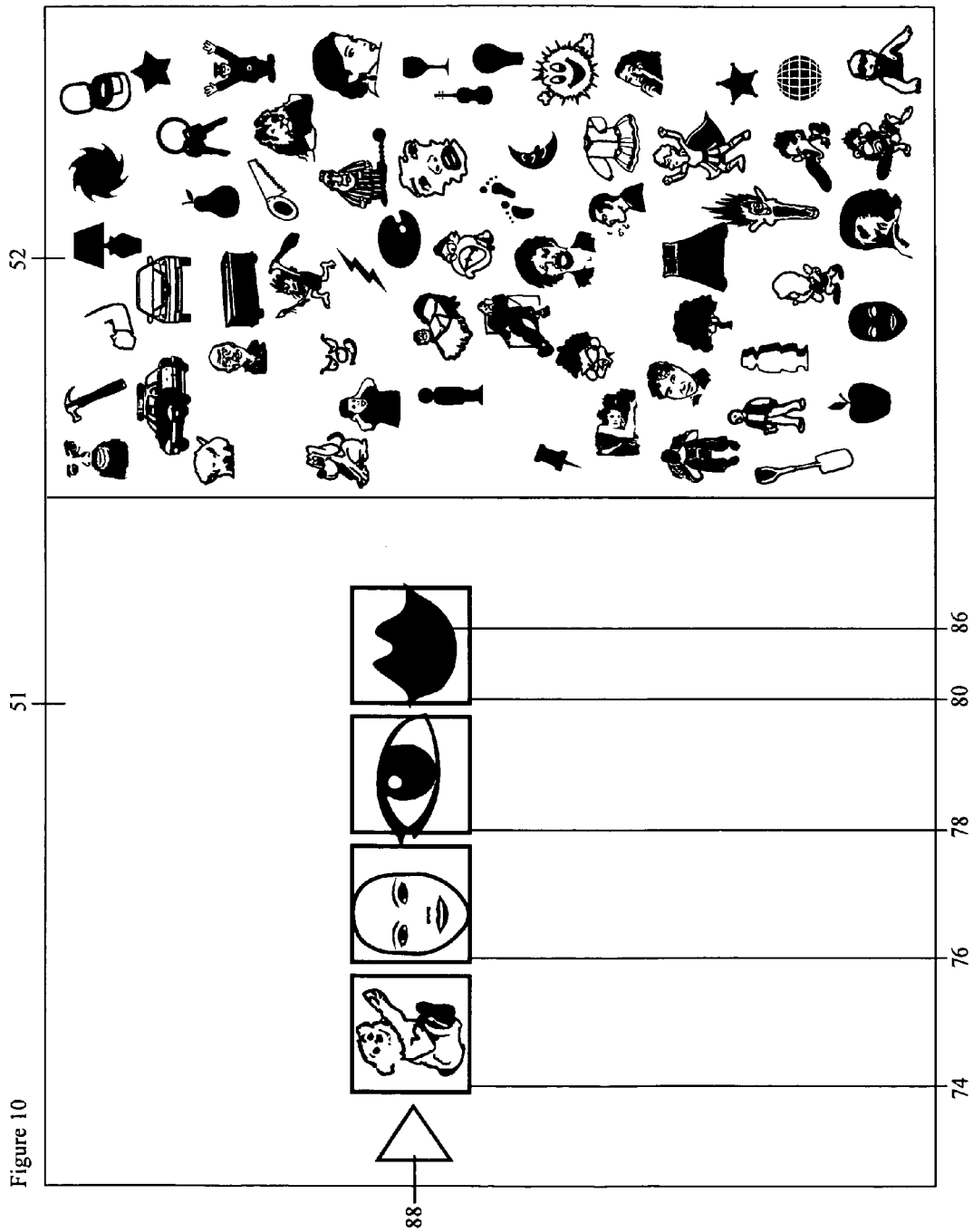
FIG. 10 displays an icon placement by the cursor within the fourth square within the diagnostic field of the user interface.

Referring now to FIG. 10, an icon such as lips icon 86 from icon field 52 is placed in any square in diagnostic field 51, for example, onto square 80; launching play button 88 (Note: Play button is launched after four squares in any order have been filled with icons).

Figure 11:
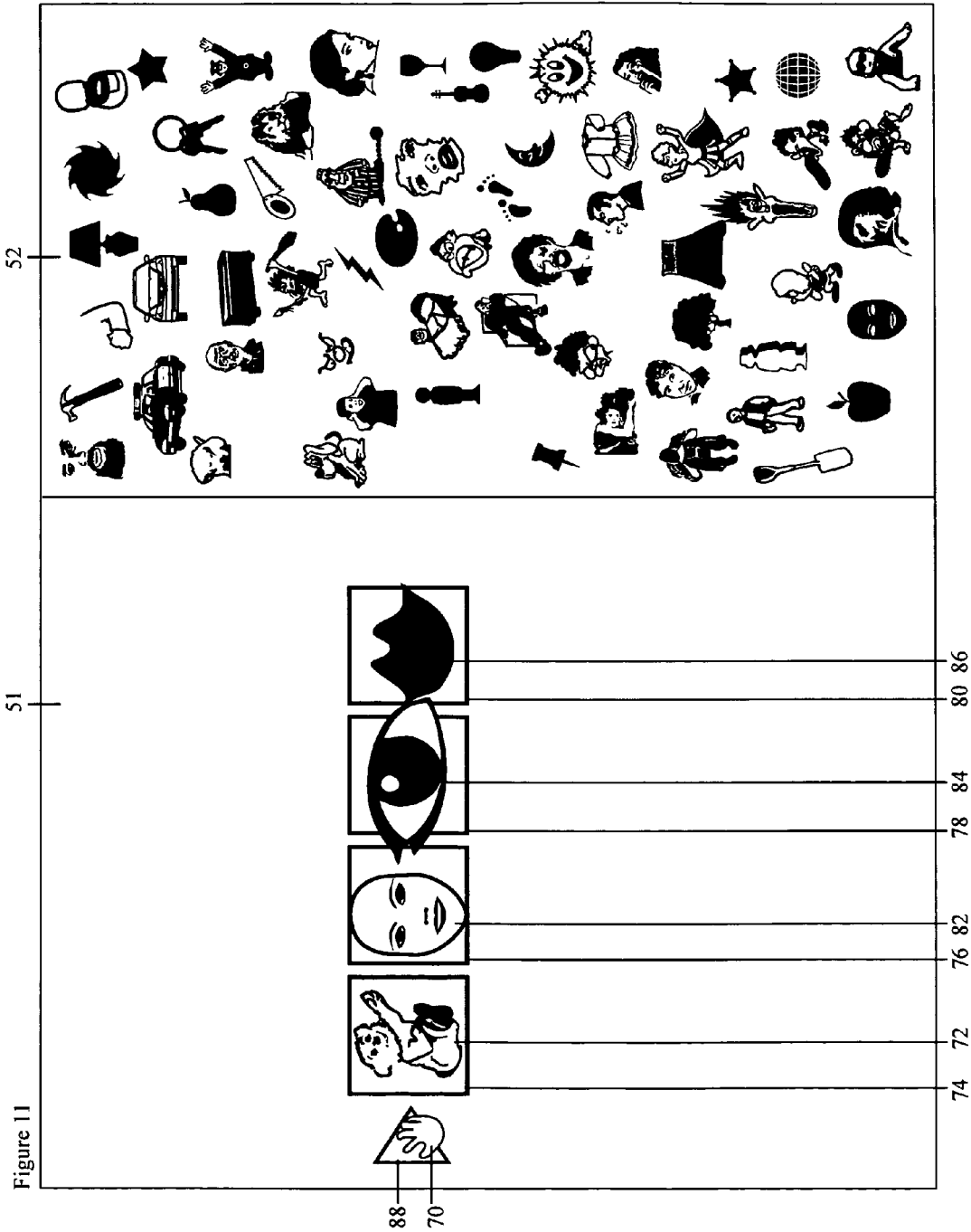
FIG. 11 displays the cursor on the first play button and the enlarged "played" icon in the third square within the diagnostic field of the user interface.

Referring now to FIG. 11, cursor 70 encounters play button 88 which plays the icons 72, 82, 84 and 86 respectively in squares 74, 76, 78 and 80 so that one by one icons 72, 82, 84 and 86 enlarge and emit their sound sounds.

Figure 12:
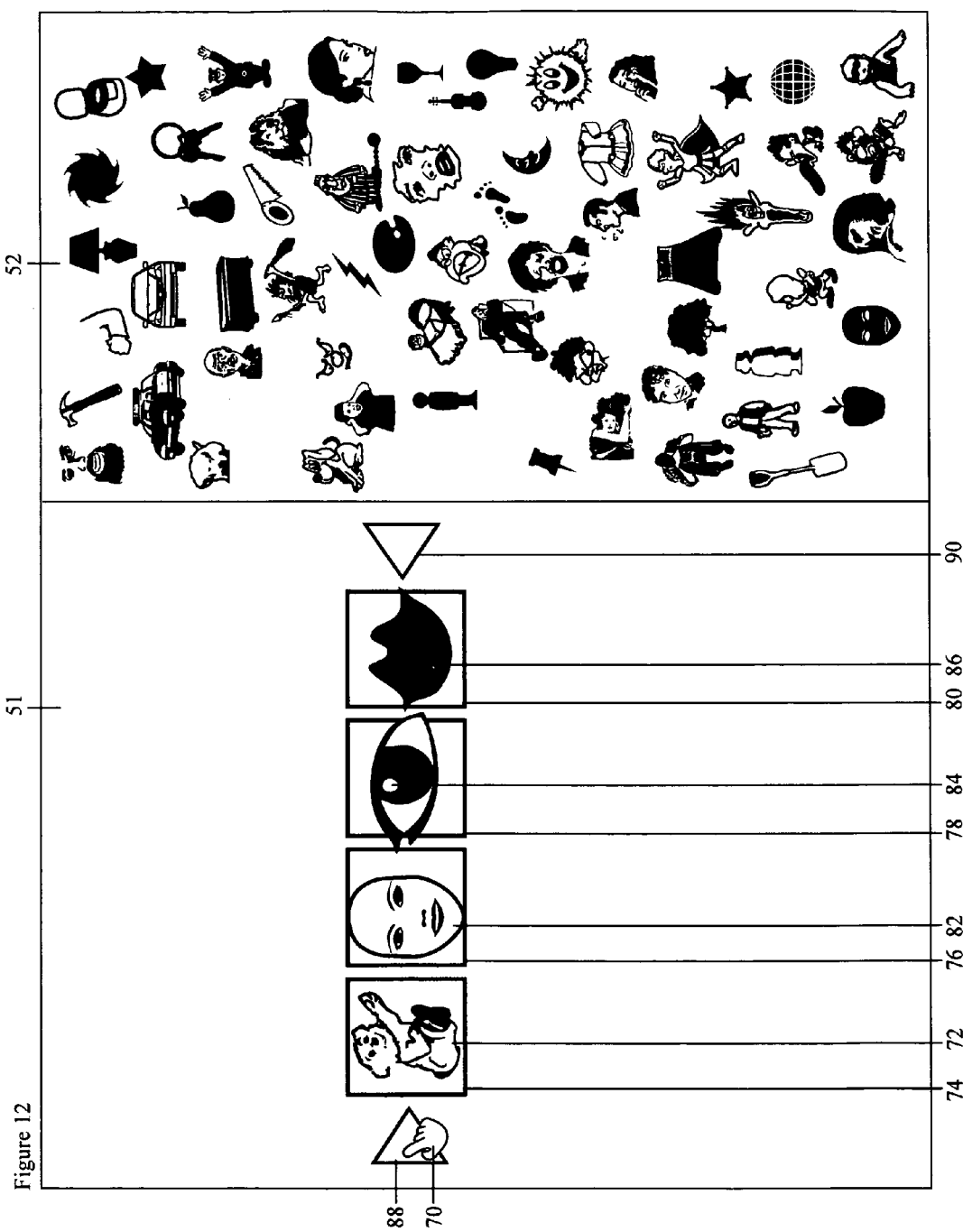
FIG. 12 displays the cursor on the first play button, and the appearance of the second play button within the diagnostic field of the user interface.

Referring now to FIG. 12, the played sequence of icons 74, 76, 78 and 80 launches play button 90.

Figure 13:
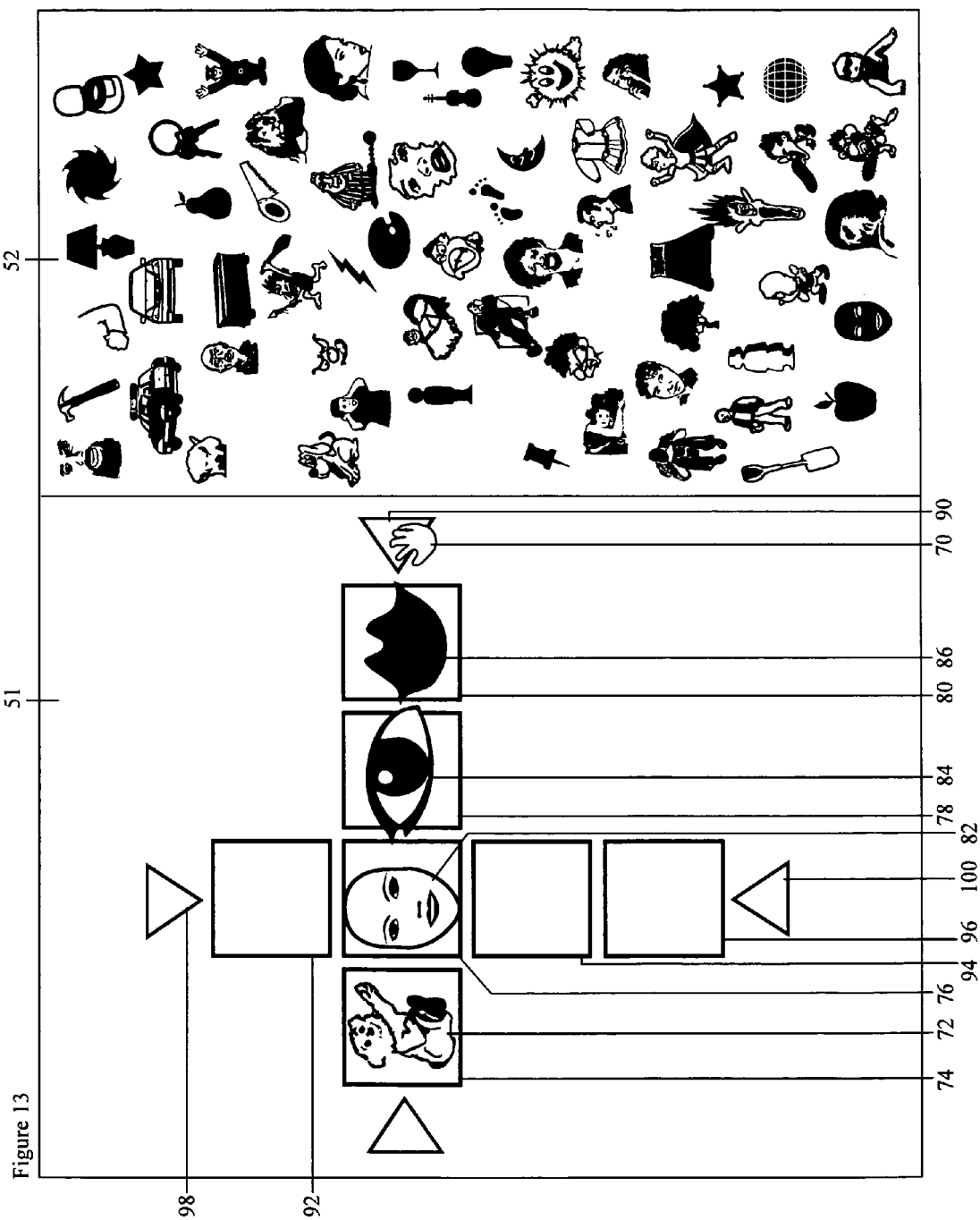
FIG. 13 displays three squares placed vertically and two new play buttons within the diagnostic field of the user interface.

Referring now to FIG. 13, cursor 70 encounters play button 90 which launches play buttons 98 and 100 and squares 92, 94 and 96.

Figure 14:
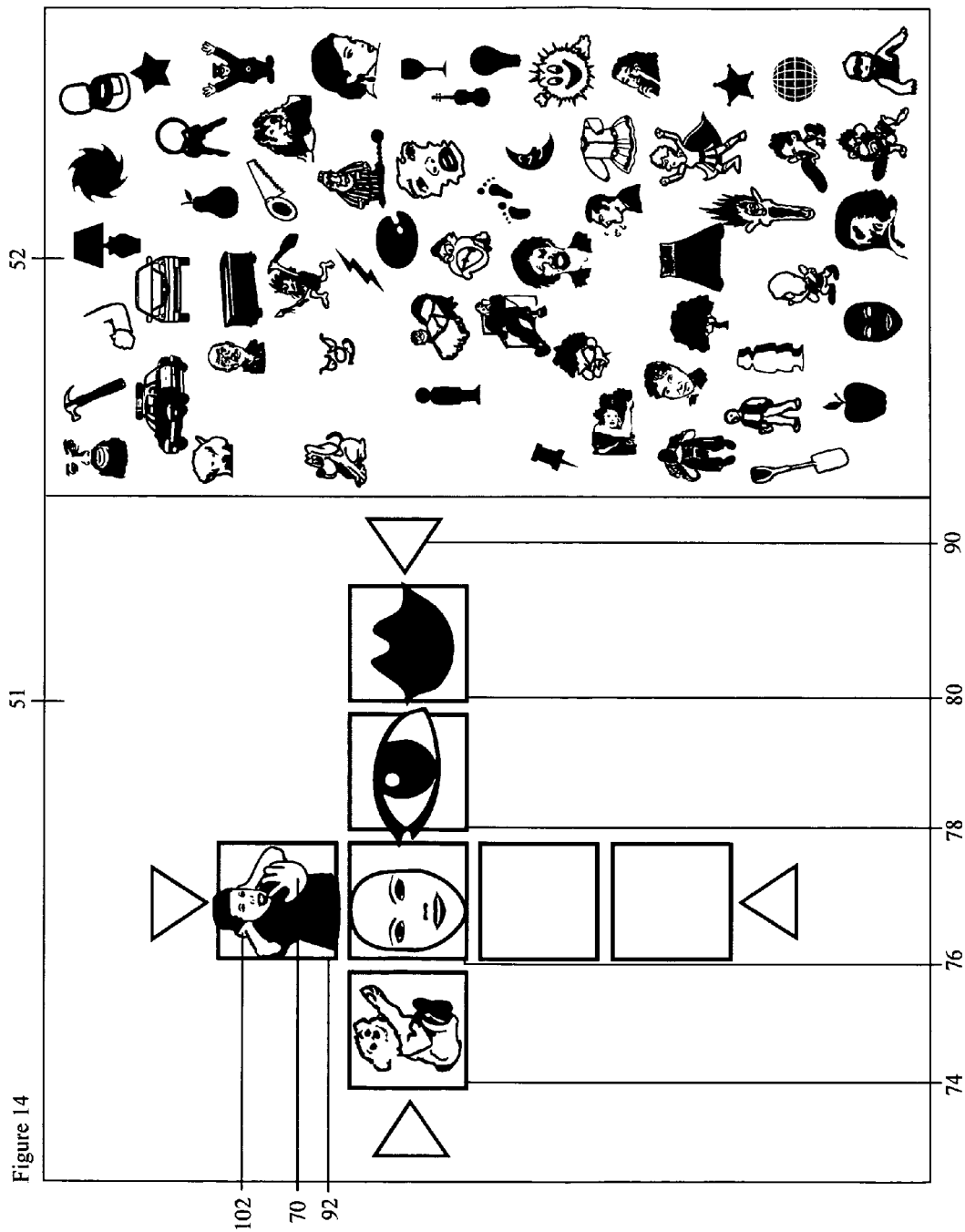
FIG. 14 displays an icon placement by the cursor within the topmost square within the diagnostic field of the user interface.

Referring now to FIG. 14, cursor 70 places icon such as covered ears icon 102 on a square in diagnostic field 51 on, for example, square 92.

Figure 15:
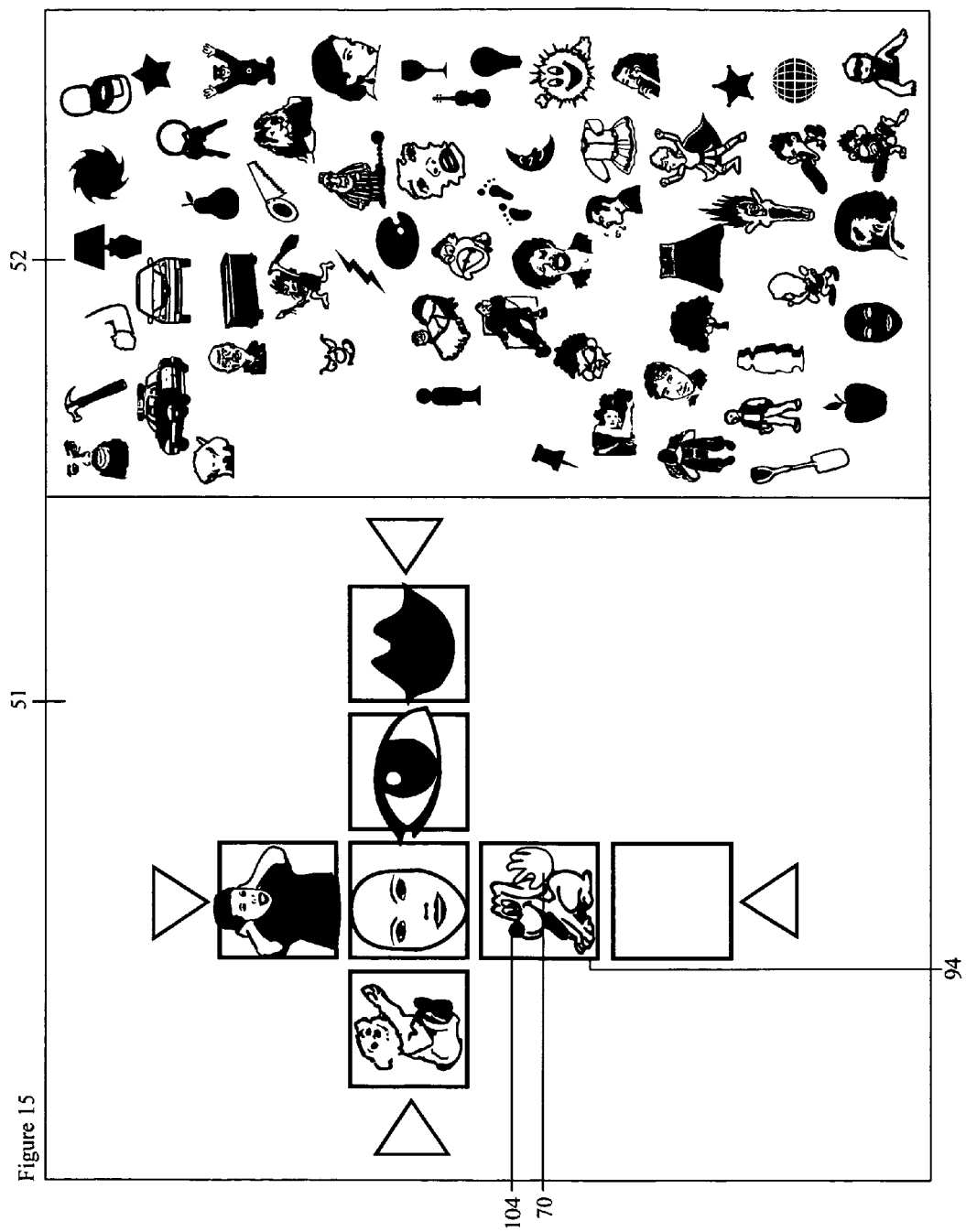
FIG. 15 displays an icon placement by the cursor within the second-from-the-bottom square within the diagnostic field of the user interface.

Referring now to FIG. 15, cursor 70 places icon such as cartoon dog icon 104 from icon field 52 onto a square in diagnostic field 51, for example, square 94.

Figure 16:
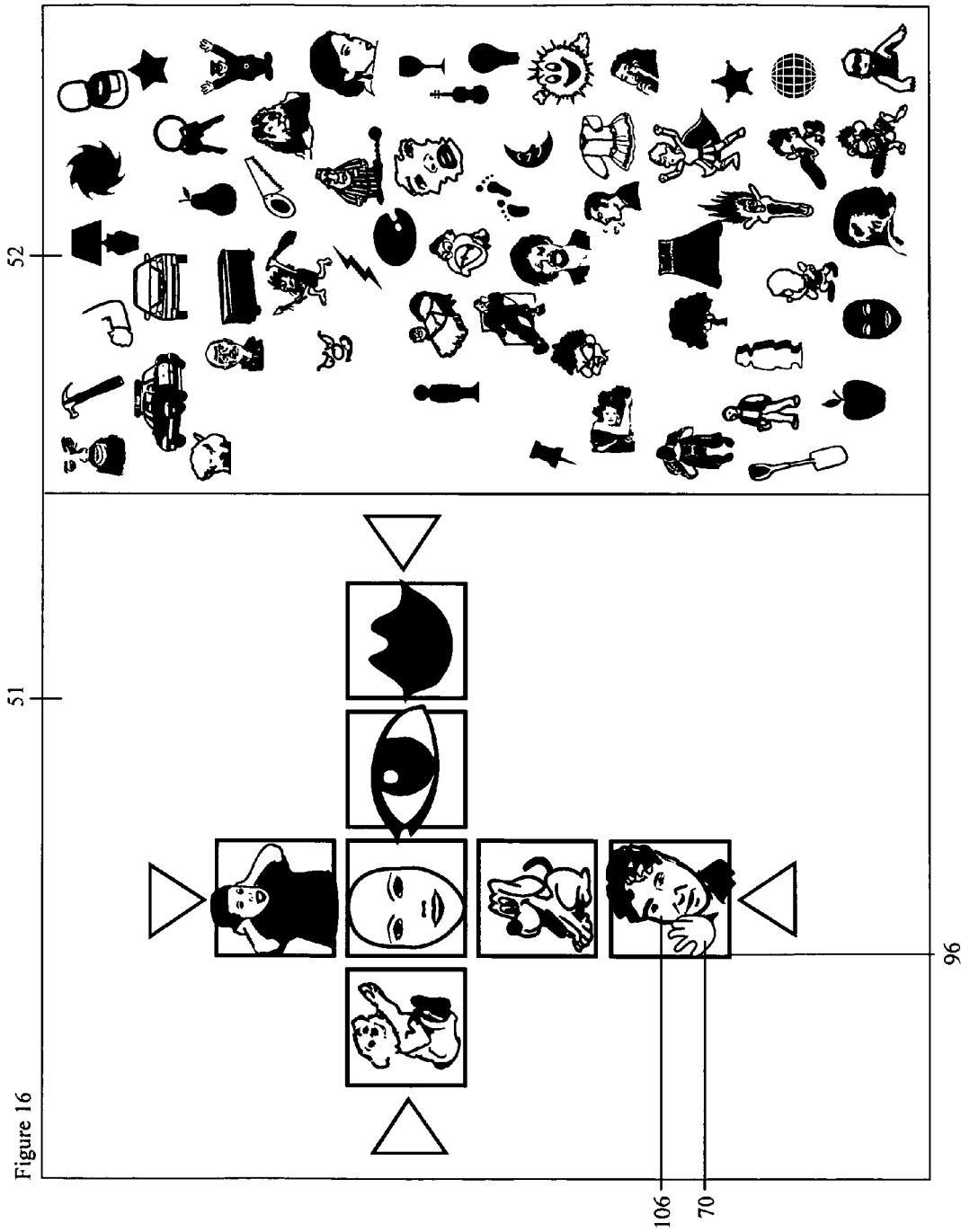
FIG. 16 displays an icon placement by the cursor within the bottom square within the diagnostic field of user interface.

Referring now to FIG. 16, cursor 70 places icon such as adult male icon 106 from icon field 52 onto a square in diagnostic field 51, for example, square 96.

Figure 17:
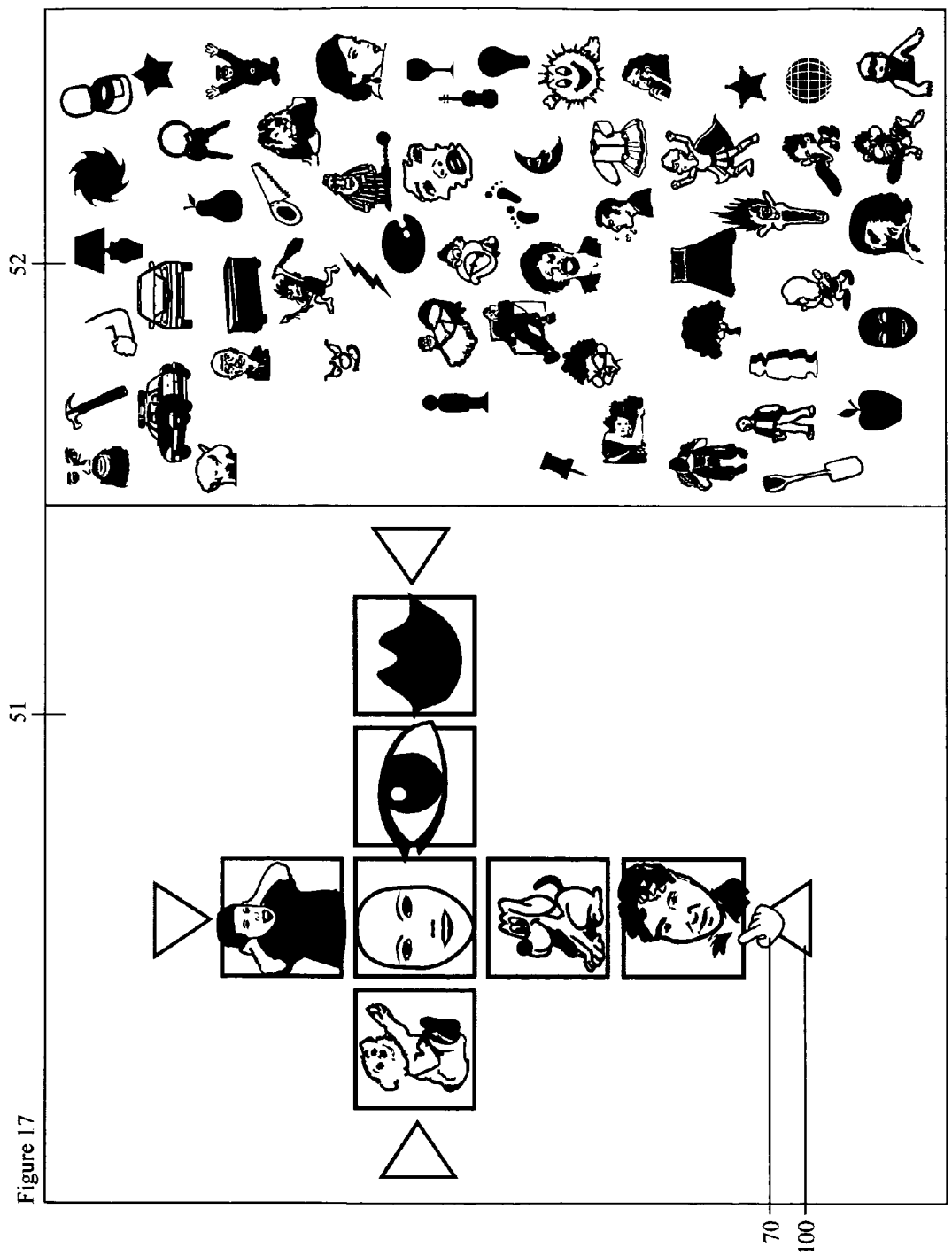
FIG. 17 displays the cursor on the lowest play button within the diagnostic field of user interface.

Referring now to FIG. 17, cursor 70 encounters play button 100.

Figure 18:
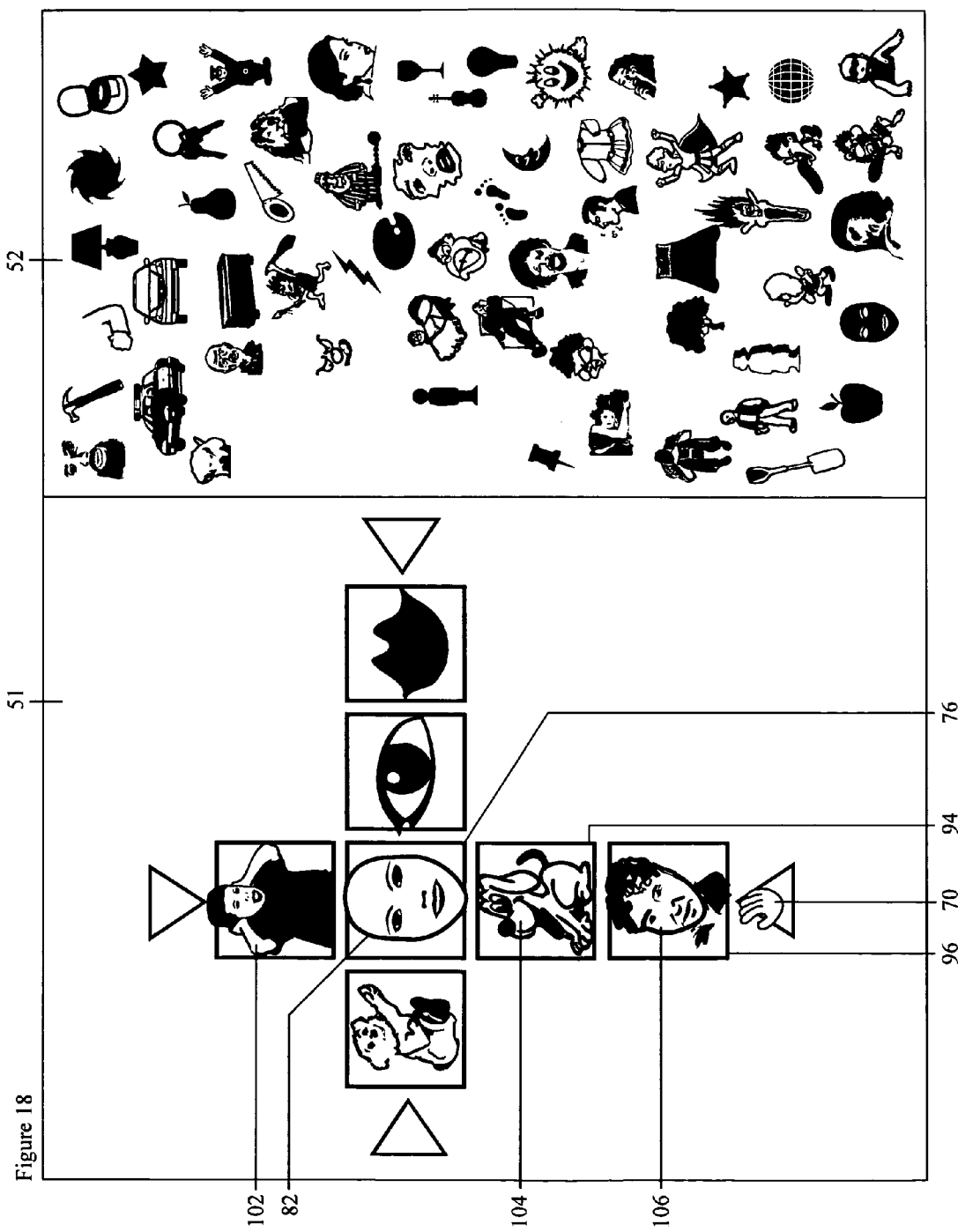
FIG. 18 displays the cursor on the lowest play button and the enlarged "played" icons in the vertical row above the cursor within the diagnostic field of user interface.

Referring now to FIG. 18, icon sequence 102, 82, 104 and 106 sequentially enlarge, and respectively emit their sounds. A user is also able to play a sequence of the icons the user has placed by pointing to the play button and is able to move selected icons from one square to another.

Figure 19:
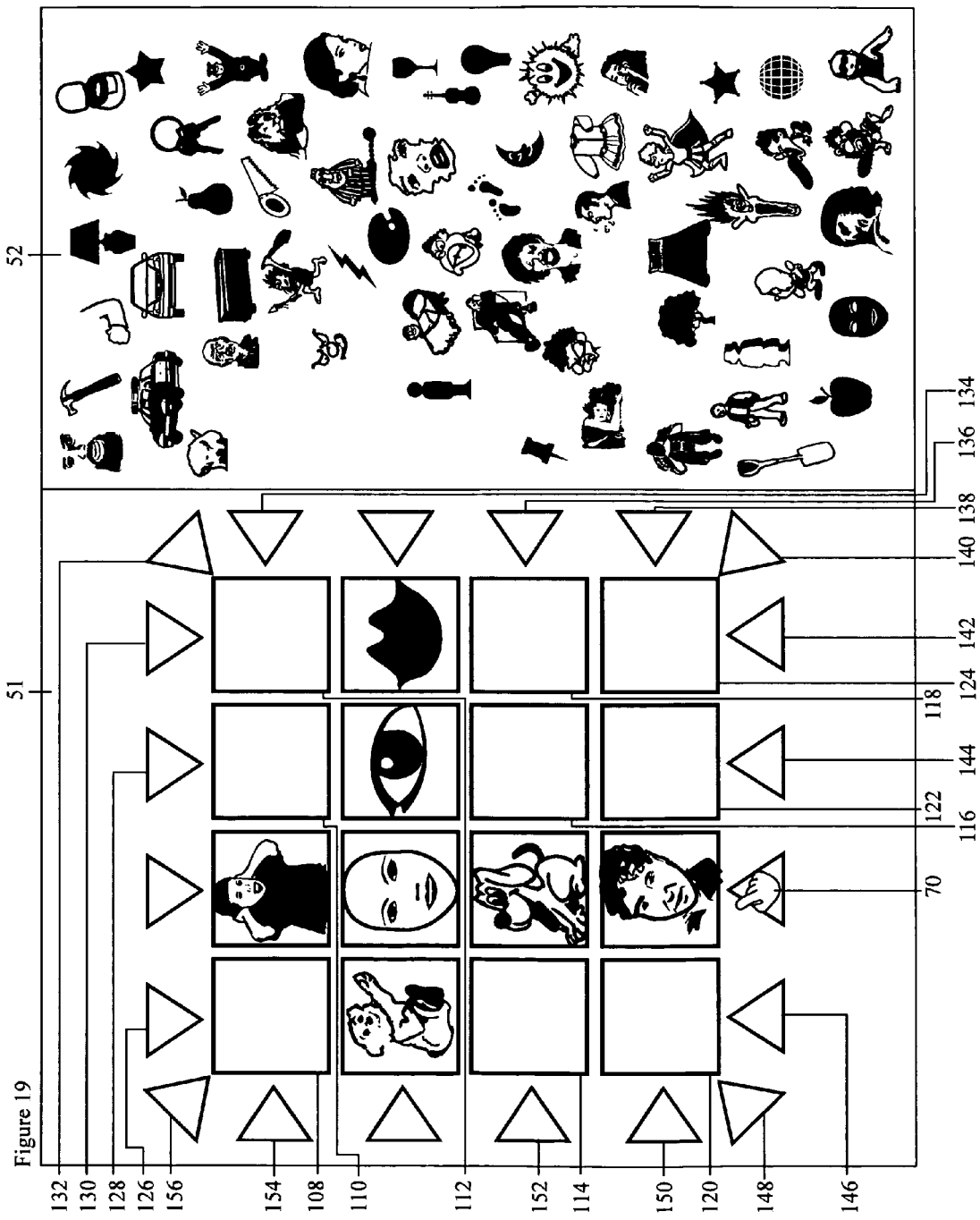
FIG. 19 displays the total number of squares and play buttons possible within the diagnostic field of user interface.

Referring now to FIG. 19, additional squares 108, 110, 112, 114, 116, 118, 120, 122 and 124 appear. Additional play buttons 126, 128, 130, 132, 134, 136, 138, 140, 142, 144, 146, 148, 150, 152, 154, 156 also appear. User can use cursor 70 to encounter any icon in icon field 52 and move it to any square.

Figure 20:
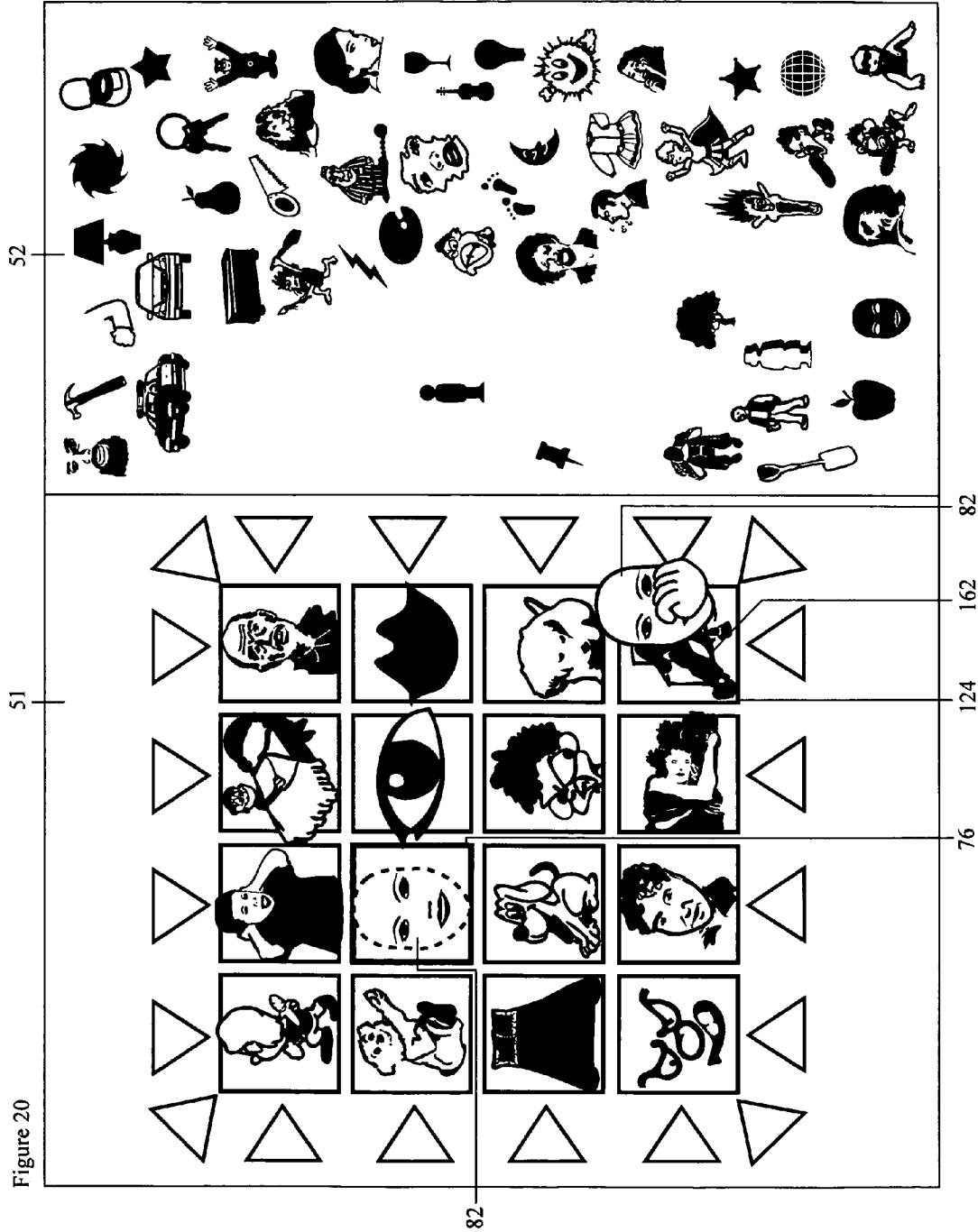
FIG. 20 displays an example of one icon being replaced by another icon within the diagnostic field of user interface.

Referring now to FIG. 20, user is able to remove any relevant icons such as face icon 82 from square 76 and place it in any relevant square such as square 124, displacing slouching man icon 162 which appears back in icon field 52.

The choice and place and point value of the chosen icons data 60 are tabulated, scored and saved in database 62.

The still and video digital camera 18 is attached to both the scanner 20 and the microprocessor 12 and allows pictures of the user/patient or chosen objects to be shot, then scanned into the microprocessor 12. It also allows the timed tracking of the user's facial expression as the user goes through the program 30.

The scanner 20 is attached to the digital camera 18 and to the microprocessor 12 and enables digital pictures of the user/patient or chosen objects to be transferred to icon field 52 as object-icons.

The microphone 16 is attached to the microprocessor 16 and enables statements or sounds from the user/patient or the objects to be recorded and then transferred to the icon-object on icon field 52.

As to a further discussion of the manner of usage and operation of the present system, the same should be apparent from the above description. Accordingly, no further discussion relating to the manner of usage and operation will be provided.

Additional Embodiments

Just prior to the session, the attached camera 18 and scanner 20 let therapist quickly and easily take a picture of the user, those items, objects or representations significant to him/her and make them into icons placed to be placed in icon field 52 for the subject to pick out or choose at will and thus getting objects/items of significance to him/her into the story.

The same camera 18 mounted over display 15 provides a timed "running video" of the subject's facial expression and direction of gaze as he/she works through the system constructing the "story".

The opening screen FIG. 4 without the four squares 74, 76 78 80: that is, the user/patient can simply drag and drop icons of his or her choice out of icon field 52 at will, in and with no particular order.

Modular: easily exchangeable icons reflecting the objects, locations or experiences in the particular environment of the subject (e.g., subject saw father shoot mother with a gun), or community events (e.g., fire, flood, earthquake disaster).

Interface with a 3-d projector: Project FIG. 4 on display 15 over pulsing light source (as per the light box of Stephen Vazquez, PhD) so children, adults can non-verbally tell their story as the light waves and frequencies evoke receptive mental states.

With respect to the above description, then, it is to be realized that the optimum dimensional relationships for the parts of the system, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present system.

Therefore, the foregoing is considered as illustrative only of the principles of the system. Further, since numerous modifications and changes will readily occur to those skilled in the art, it is not desired to limit the system to the exact construction and operation shown and described, and accordingly, all suitable modifications and equivalents may be resorted to, falling within the scope of the system.

Defined in detail, the present invention is a computer-aided psychological and diagnosis and treatment system to enable a user to express information about a past traumatic event, comprising: (a) a microprocessor connected to a storage element having a computer database, a display, a microphone, a camera, a scanner, a keyboard and a mouse which is used as a pointing device; (b) a diagnostic and treatment software which is launched on the microprocessor which enables a screen to become visible on said display, the screen having a multiplicity of object icons appearing thereon, the mouse having a cursor which can selectively point to an individual one of the object icons to create an encounter, the initiation of an encounter causing a timer in the storage element to cause the storage element to record and retain in the computer database information such as the time of the encounter, the duration of the encounter, the direction of movement at the encounter, and the direction of movement at termination of the encounter; (c) the system enabling the user to explore the object icon field by causing the cursor to move within the object icon field and select an individual object icon and when the cursor encounters the selected object icon, the selected object icon enlarges and emits a unique sound, and concurrently a diagnostic field appears on the screen with a multiplicity of squares appearing on the screen so that the user can move the selected object icon into a selected square on the diagnostic screen; (d) the process of step "c" repeated until a multiplicity of object icons have been selected and respectively placed within a square of the diagnostic screen at which time a user-clicked play button causes each of the selected icons to enlarge and then emit a sound in sequence, to thereby provide a visual picture of a story the user is telling; (e) a scanner attached to the camera and the microprocessor, the camera taking pictures of the user as the user is performing steps "c" and "d" which pictures are scanned into the microprocessor, the microprocessor transferring selected photographs of the user into the area of the screen containing the object icons which thereby triggers the user to perform additional steps "c" and "d" when the user sees the user's picture associated with the object icons, the pictures stored in the computer database; (f) the microphone connected to the microprocessor enabling statements or sounds from the user and/or the selected objects in the display field to be recorded and then transferred to the object icon field and also stored in the computer database; and (g) the record of the selected object icons, the order in which they are placed in the display field, their sequence of play and all other visual and vocal emissions of the user and the information about the encounters all being stored in the computer database to provide a complete record which enables a mental health professional to analyze a story the user is telling to determine information about the past traumatic event the user went through.

Defined broadly, the present invention is a computer-aided psychological and diagnosis and treatment system to enable a user to express information about a past traumatic event, comprising: (a) a microprocessor connected to a storage element having a computer database, a display providing a screen and a means for pointing to images on the screen; (b) a diagnostic and treatment software which is launched on the microprocessor which enables a screen to become visible on said display, the screen having a multiplicity of icons appearing thereon, the pointing means enabling the user to selectively point to an individual one of the icons to create an encounter which is stored in the computer database; (c) the system enabling the user to explore the field of icons by causing the pointing means to move within the field of icons and select an individual icon and when the pointing means encounters the selected icon, the user can move the selected icon into a selected one of a multiplicity of locations on another part of the screen; (d) the process of step "c" repeated until a multiplicity of icons have been selected and respectively placed within a location on the screen, the user being able to then play a sequence of the icons the user has placed by pointing to the play button to thereby provide a visual picture of a story the user is telling; (e) the user being able to move selected icons from one location to another; (f) the record of the selected icons, the order in which they are placed on a location on the screen and all other information about the encounters all being stored in the computer database to provide a complete record which enables a mental health professional to analyze a story the user is telling to determine information about the past traumatic event the user went through.

Defined more broadly, the present invention is a psychological diagnosis and treatment system comprising a computer implemented method which elicits, extracts, records and archives information created by a user interacting with visual images displayed on a computer screen to enable the user to express through a series of computer generated visual images a story about a disturbing event previously experienced by the user.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A computer-aided psychological and diagnosis and treatment system to enable a user to express information about a past traumatic event, comprising:
   a. a microprocessor connected to a storage element having a computer database, a display, a microphone, a camera, a scanner, a keyboard and a mouse which is used as a pointing device;
   b. a diagnostic and treatment software which is launched on the microprocessor which enables a screen to become visible on said display, the screen having a multiplicity of object icons appearing thereon, the mouse having a cursor which can selectively point to an individual one of the object icons to create an encounter, the initiation of an encounter causing a timer in the storage element to cause the storage element to record and retain in the computer database information comprising the time of the encounter, the duration of the encounter, the direction of movement at the encounter, and the direction of movement at termination of the encounter;
   c. the system enabling the user to explore the object icon field by causing the cursor to move within the object icon field and select an individual object icon and when the cursor encounters the selected object icon, the selected object icon enlarges and emits a unique sound, and concurrently a diagnostic field appears on the screen with a multiplicity of squares appearing on the screen so that the user can move the selected object icon into a selected square on the diagnostic screen;
   d. the process of step "c" repeated until a multiplicity of object icons have been selected and respectively placed within a square of the diagnostic screen at which time a user-clicked play button causes each of the selected icons to enlarge and then emit a sound in sequence, to thereby provide a visual picture of a story the user is telling;
   e. a scanner attached to the camera and the microprocessor, the camera taking pictures of the user as the user is performing steps "c" and "d" which pictures are scanned into the microprocessor, the microprocessor transferring selected photographs of the user into the area of the screen containing the object icons which thereby triggers the user to perform additional steps "c" and "d" when the user sees the user's picture associated with the object icons, the pictures stored in the computer database;
   f. the microphone connected to the microprocessor enabling statements or sounds from the user and/or the selected objects in the display field to be recorded and then transferred to the object icon field and also stored in the computer database; and
   g. the record of the selected object icons, the order in which they are placed in the display field, their sequence of play and all other visual and vocal emissions of the user and the information about the encounters all being stored in the computer database to provide a complete record which enables a mental health professional to analyze a story the user is telling to determine information about the past traumatic event the user went through.

2. A computer-aided psychological and diagnosis and treatment system to enable a user to express information about a past traumatic event, comprising:
   a. a microprocessor connected to a storage element having a computer database, a display providing a screen and a means for pointing to images on the screen;
   b. a diagnostic and treatment software which is launched on the microprocessor which enables a screen to become visible on said display, the screen having a multiplicity of icons appearing thereon, the pointing means enabling the user to selectively point to an individual one of the icons to create an encounter which is stored in the computer database;
   c. the system enabling the user to explore the field of icons by causing the pointing means to move within the field of icons and select an individual icon and when the pointing means encounters the selected icon, the user can move the selected icon into a selected one of a multiplicity of locations on another part of the screen;
   d. the process of step "c" repeated until a multiplicity of icons have been selected and respectively placed within a location on the screen, the user being able to then play a sequence of the icons the user has placed by pointing to the play button to thereby provide a visual picture of a story the user is telling;

e. the user being able to move selected icons from one location to another;

f. the record of the selected icons, the order in which they are placed on a location on the screen and all other information about the encounters all being stored in the computer database to provide a complete record which enables a mental health professional to analyze a story the user is telling to determine information about the past traumatic event the user went through;

g. means in the storage element to record and retain in the computer database information comprising the time of the encounter, the duration of the encounter, the icon sequences played, the direction of movement at the encounter, and the direction of movement at termination of the encounter;

h. wherein upon the occurrence of an encounter, the icon enlarges and emits a unique sound; and i. a scanner attached to a camera and the microprocessor, the camera taking pictures of the user as the user is performing steps "b" and "c" which pictures are scanned into the microprocessor, the microprocessor transferring selected photographs of the user into the area of the screen containing the object icons which thereby triggers the user to perform additional steps "b" and "c" when the user sees the user's picture associated with the object icons, the pictures stored in the computer database.

3. A computer-aided psychological and diagnosis and treatment system to enable a user to express information about a past traumatic event, comprising:

a. a microprocessor connected to a storage element having a computer database, a display providing a screen and a means for pointing to images on the screen;

b. a diagnostic and treatment software which is launched on the microprocessor which enables a screen to become visible on said display, the screen having a multiplicity of icons appearing thereon, the pointing means enabling the user to selectively point to an individual one of the icons to create an encounter which is stored in the computer database;

c. the system enabling the user to explore the field of icons by causing the pointing means to move within the field of icons and select an individual icon and when the pointing means encounters the selected icon, the user can move the selected icon into a selected one of a multiplicity of locations on another part of the screen;

d. the process of step "c" repeated until a multiplicity of icons have been selected and respectively placed within a location on the screen, the user being able to then play a sequence of the icons the user has placed by pointing to the play button to thereby provide a visual picture of a story the user is telling;

e. the user being able to move selected icons from one location to another; and f. the record of the selected icons, the order in which they are placed on a location on the screen and all other information about the encounters all being stored in the computer database to provide a complete record which enables a mental health professional to analyze a story the user is telling to determine information about the past traumatic event the user went through;

g. means in the storage element to record and retain in the computer database information comprising the time of the encounter, the duration of the encounter, the icon sequences played, the direction of movement at the encounter, and the direction of movement at termination of the encounter;

h. wherein upon the occurrence of an encounter, the icon enlarges and emits a unique sound;

i. a scanner attached to a camera and the microprocessor, the camera taking pictures of the user as the user is performing steps "b" and "c" which pictures are scanned into the microprocessor, the microprocessor transferring selected photographs of the user into the area of the screen containing the object icons which thereby triggers the user to perform additional steps "b" and "c" when the user sees the user's picture associated with the object icons, the pictures stored in the computer database; and j. a microphone connected to the microprocessor enabling statements or sounds from the user and/or sounds emitted by the icons to be recorded and stored in the computer database.

* * * * *